United States Patent [19]
Lee et al.

[11] Patent Number: 5,602,341
[45] Date of Patent: Feb. 11, 1997

[54] TEST FIXTURE FOR SPOT WELDS

[75] Inventors: Yung-Li Lee, Troy; Timothy Wehner, Auburn Hills; Thomas Morrissett, Troy; Eric Pakalnins, Hartland; Ming-Wei Lu, Ann Arbor, all of Mich.

[73] Assignee: Chrysler Corporation, Auburn Hills, Mich.

[21] Appl. No.: 643,902

[22] Filed: May 7, 1996

[51] Int. Cl.⁶ ..................................................... G01N 3/20
[52] U.S. Cl. .............................................. 73/850; 73/856
[58] Field of Search ............................. 73/827, 842, 850, 73/856

[56] References Cited

U.S. PATENT DOCUMENTS

| | | | |
|---|---|---|---|
| 4,012,947 | 3/1977 | Tiegel | 73/842 |
| 4,380,174 | 4/1983 | Tanenbaum | 73/842 |
| 4,573,360 | 3/1986 | Yoneda | 73/850 |
| 4,677,856 | 7/1987 | Fischer | 73/850 |
| 4,893,944 | 1/1990 | Leroux | 73/827 X |
| 5,291,423 | 3/1994 | Roosli | 73/850 X |
| 5,415,047 | 5/1995 | Maciejewski et al. | 73/850 |

FOREIGN PATENT DOCUMENTS

| | | | |
|---|---|---|---|
| 4250334 | 9/1992 | Japan | 73/850 |
| 1093942 | 5/1984 | U.S.S.R. | 73/850 |
| 1415138 | 8/1988 | U.S.S.R. | 73/850 |
| 1479845 | 5/1989 | U.S.S.R. | 73/850 |

*Primary Examiner*—Elizabeth L. Dougherty
*Attorney, Agent, or Firm*—Edward A. Craig

[57] ABSTRACT

A fixture for testing the strength of a resistance spot weld connecting two test strips comprises two identical clamping frames, each having releasable clamps for gripping and holding one of the test strips. A pull bar is mounted on each clamping frame in any one of several selected angular positions. The pull bars are aligned with one another and then grasped by a pulling mechanism to apply a separating force on the two strips. The arrangement is such that the line of the separating force passes through the weld.

6 Claims, 5 Drawing Sheets

TEST FIXTURE FOR SPOT WELDS

FIELD OF THE INVENTION

This invention relates generally to test fixtures and more particularly to a fixture for testing the strength of a resistance spot weld.

BACKGROUND AND SUMMARY

Resistance spot welding is widely used in industry. In the automotive industry, the ultimate strength performance of resistance spot welds is a critical factor in design, particularly as a result of the need for vehicle weight reduction and downgaging of sheet metals (downgaging affects the strength of a resistance spot weld). What is needed is a quick and effective means for determining the ultimate strength capacity of spot welds under different stress conditions, to enable engineers to determine the number of resistance spot welds needed or to check if the resistance spot welds would fail under given loading conditions.

At the present time, welded joints can be tested in tensile shear by a machine which grasps the ends of two welded test strips and pulls in opposite directions in a plane parallel to the test strips. However, a welded joint is often subjected to loads not only in shear but also perpendicular to the plane of the welded sheet metal as well as intermediate acute angles. The fixture of the present invention is designed to test the load strength of welded sheet metal strips perpendicular to the plates and also at selected intermediate acute angles.

More specifically, the fixture of this invention is designed to test the strength of a resistance spot weld connecting two overlapping test strips, the fixture comprising two identical test units each having a clamping frame for gripping one of the test strips. Pull bars are mounted on the clamping frames of the two test units in alignment with one another and in selected angular positions. A separating force is applied to the strips by a pulling mechanism attached to the pull bars. The pulling mechanism, while not part of the invention, has a means for measuring the amount of force required to cause a weld failure and thus determine the strength of the welded joint. Since the pull bars can be mounted in various different angular positions, including one position perpendicular to the test strips, it is possible to test the strength of the resistance spot weld for stress in any of several different directions to assist an engineer in determining the strength of the weld under many conditions and the number of resistance spot welds needed in a particular application.

One object of this invention is to provide a fixture for testing the strength of resistance spot welds having the foregoing features and capabilities.

Another object is to provide a test fixture which is composed of a relatively few simple parts, is rugged and durable in use, and is capable of being inexpensively manufactured and easily and quickly operated.

These and other objects, features and advantages of the invention will become more apparent as the following description proceeds, especially when considered with the accompanying drawings.

DETAILED DESCRIPTION OF THE PREFERRED EMBODIMENT

Figure 1:
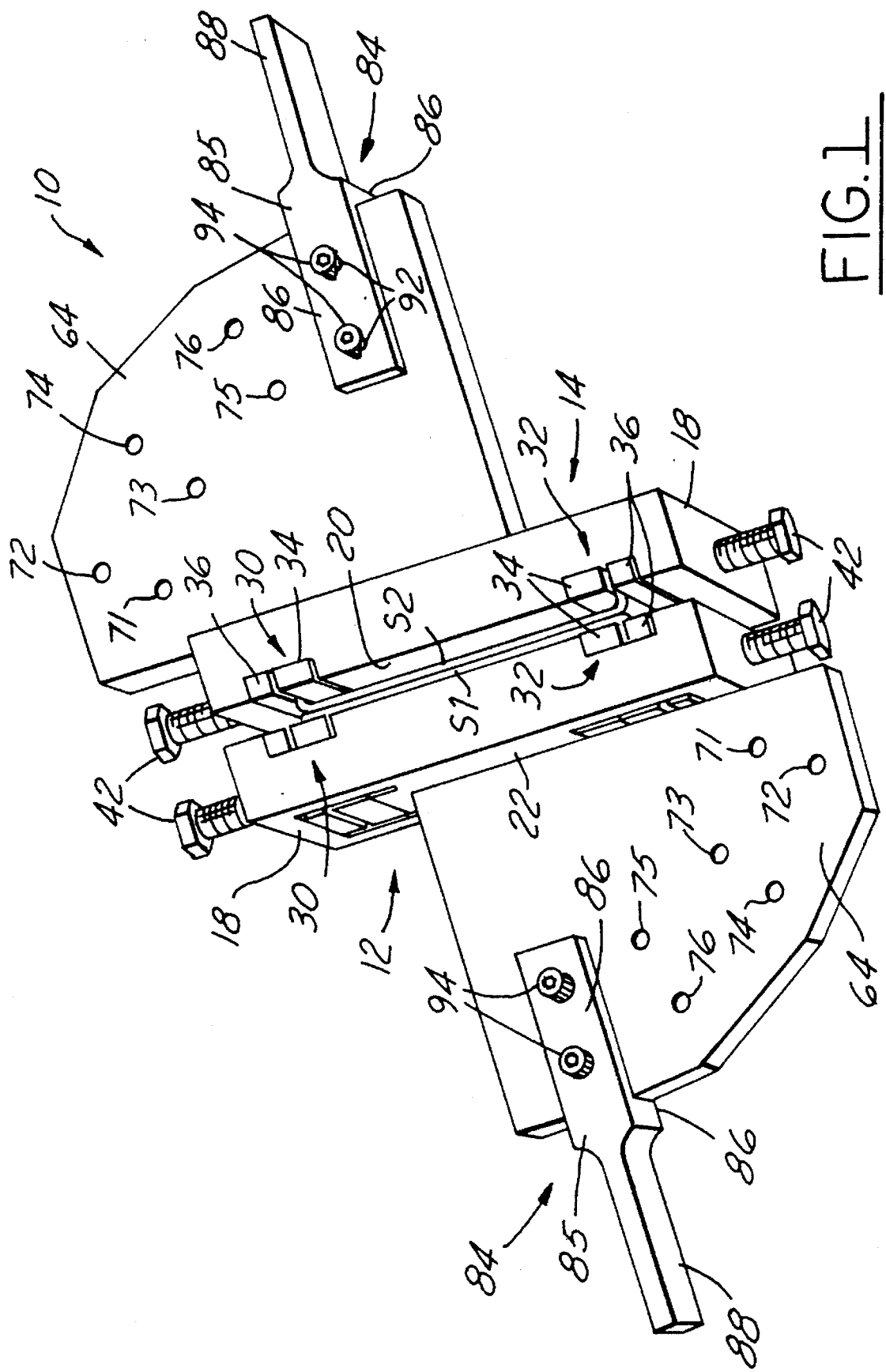
FIG. 1 is a perspective view of a test fixture constructed in accordance with this invention, showing two metal strips welded together and gripped by the two test units of the fixture.
Figure 3:
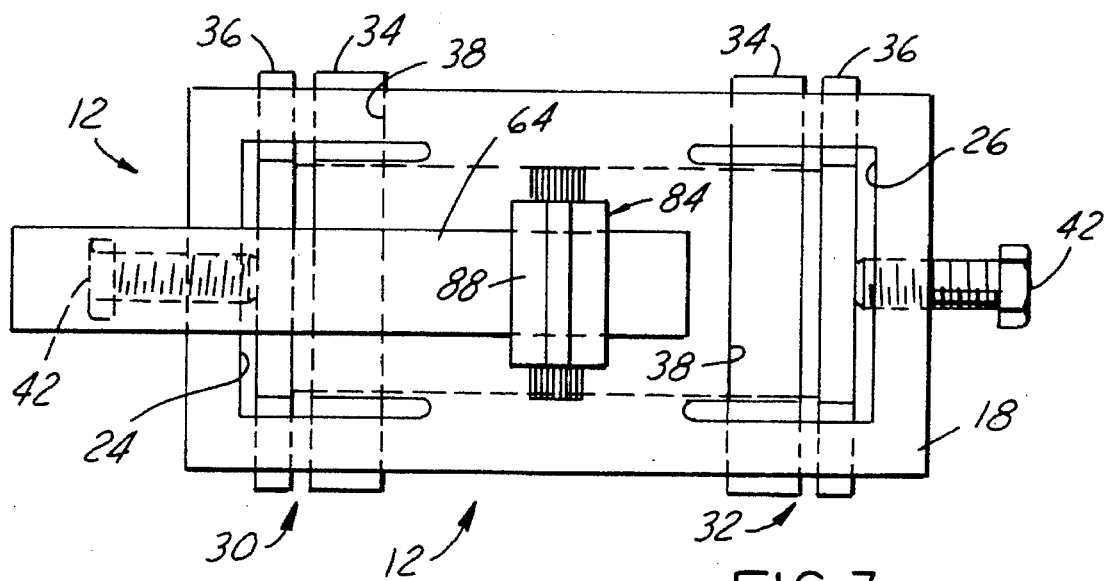
FIG. 3 is a top view of the test unit shown in FIG. 2.

Referring now more particularly to the drawings, the fixture 10 comprises two identical test units 12 and 14 which cooperate in testing the spot weld W between two parallel, overlying, rectangular metal test strips S1 and S2.

Each test unit 12,14 comprises a flat rectangular clamping frame 18 having parallel front and rear faces 20 and 22.

Figure 2:
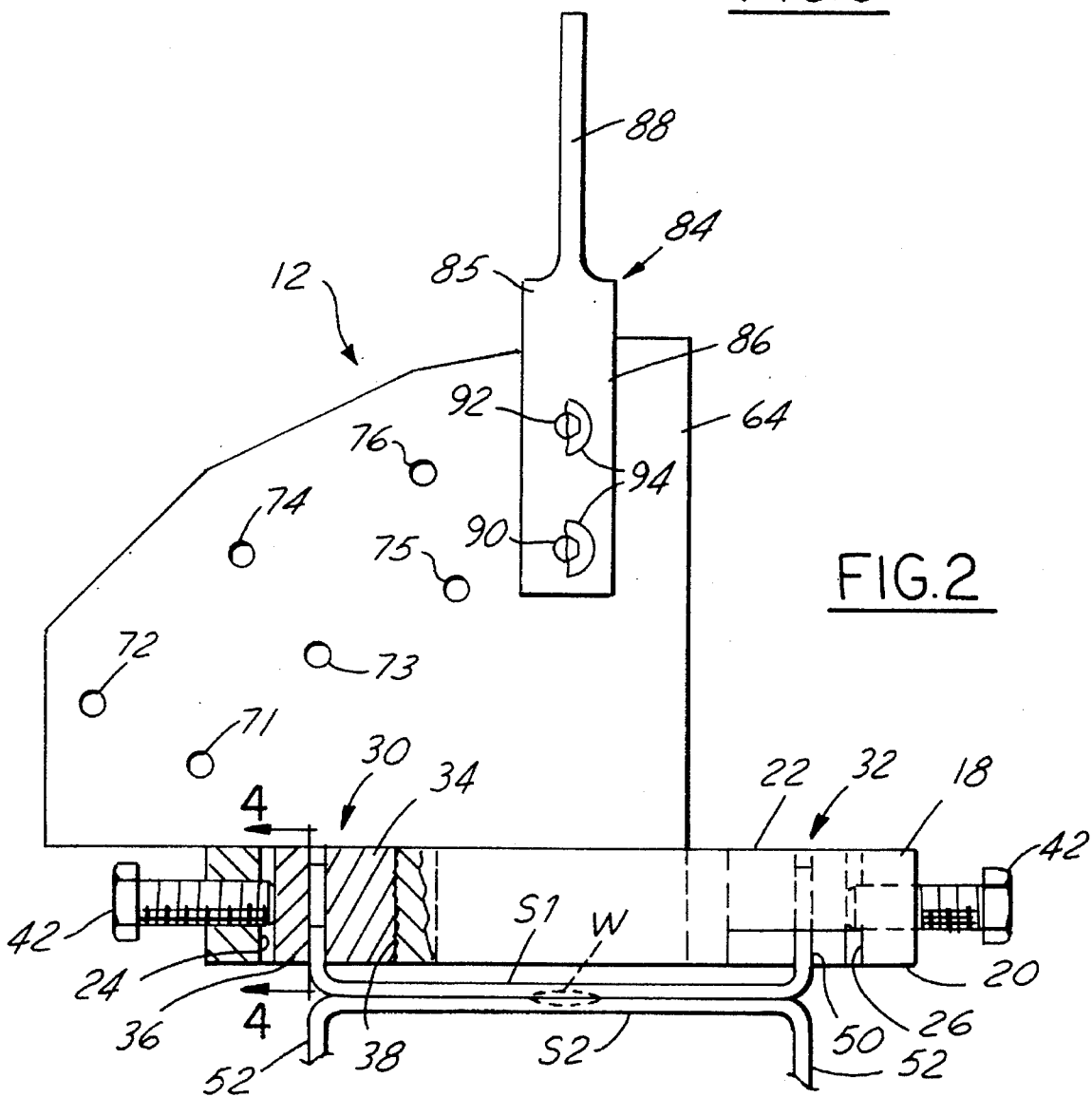
FIG. 2 is a side view of one of the test units, shown gripping one of the metal strips.
Figure 4:
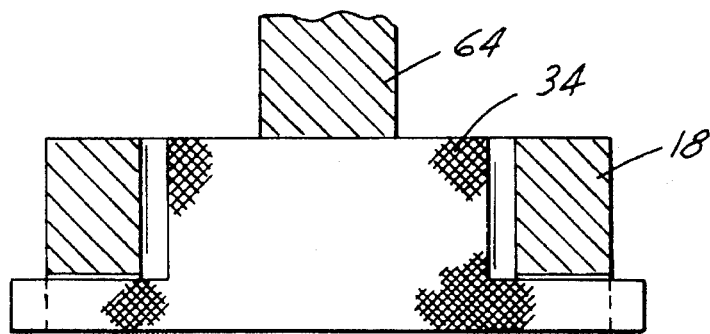
FIG. 4 is a sectional view taken on the line 4—4 in FIG.
Figure 6:
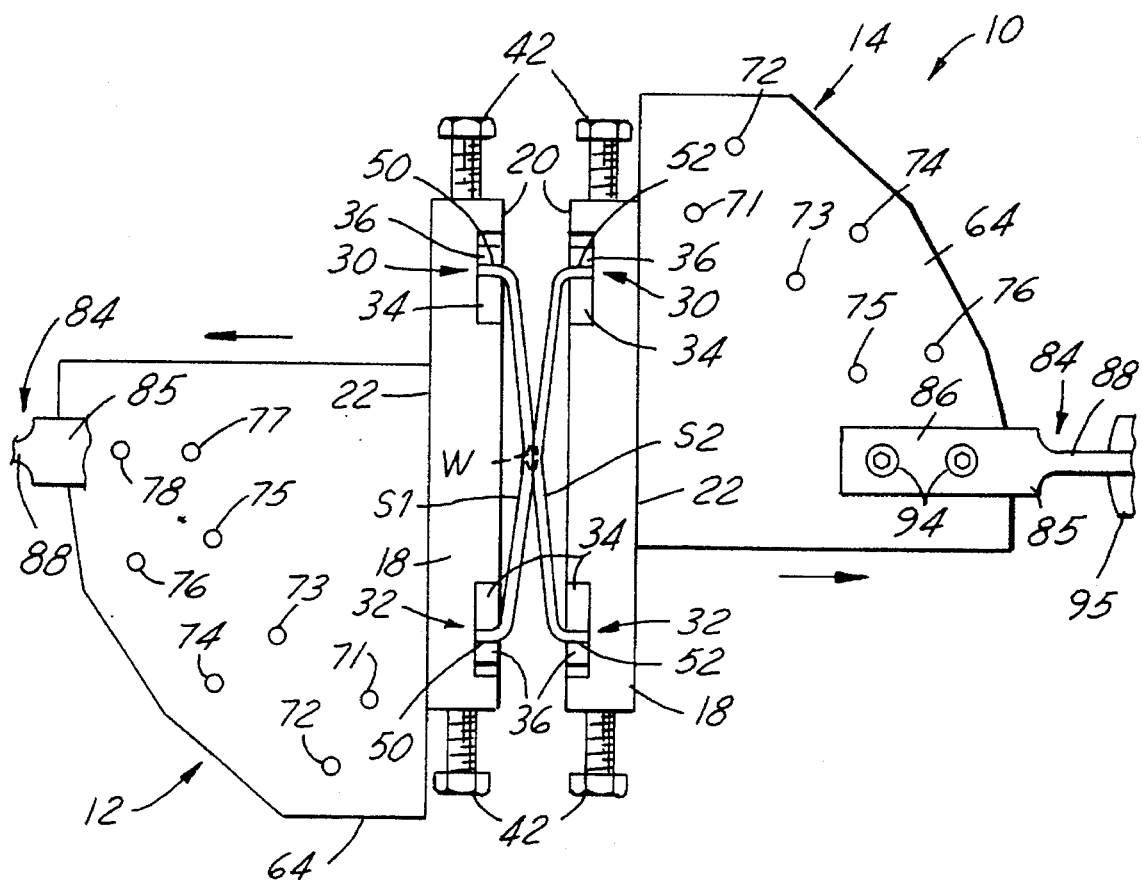
FIG. 6 is a view similar to FIG. 5, but showing the test units pulled away from one another during a test.

Each clamping frame 18 has generally rectangular openings 24 and 26 adjacent to the opposite ends for receiving clamps 30 and 32. Each clamp has two clamping inserts 34 and 36 (FIG. 2). Each of the clamping insert 34 normally seats against a transverse abutment surface 38 of the opening 24 or 26. The abutment surface 38 is serrated and provides an abutment or seat for the serrated surface of both clamping inserts 34. The other clamping insert 36 are slidable within the opening 24 or 26 toward and away from the clamping inserts 34. The opposed surfaces of clamping inserts 34 and 36 are also serrated. The clamping inserts 36 are moved into clamping engagement with the clamping inserts 34 by actuator bolts 42 which thread through the ends of the clamping frames 18. The clamping inserts 34,36 are free to fall out when the bolts are retracted, but the serrations keep them from sliding when clamping pressure is applied. Clamping inserts 34 can be replaced by other inserts having different heights. As will be appreciated from the FIG. 2 shown, varying the height of the inserts 34 will result in decreasing or increasing the length of the test strips which may be tested because of the change in distance between the pair of inserts in each clamping frame 18.

The main body portions of the metal strips S1 and S2 are flat and overlie one another. The outer ends of strip S1 are turned 90° in one direction to provide flanges 50. The outer ends of the strip S2 are bent 90° in the opposite direction to provide flanges 52. The main body portion of strip S1 extends along the front face 20 of the clamping frame 18 of test unit 12 and the main body portion of the strip S2 extends along the front face 20 of the clamping frame of test unit 14. The flanges 50 of strip S1 are clamped by the clamps 30 and 32 of the frame 18 of test unit 12 and the flanges 52 of the strip S2 are clamped by the clamps 30 and 32 of the clamping frame of test unit 14. The weld W connects the main body portions of the strips S1 and S2 midway between the flanged ends thereof, thereby creating the test specimen.

Clamping frame 18 of each test unit has a lock plate 64 rigidly secured as by welding to the rear face 22 thereof. The lock plates 64 are perpendicular to the clamping frames 18, are located midway between the opposite side edges of the clamping frames, and extend lengthwise of the clamping frames.

Figure 5:
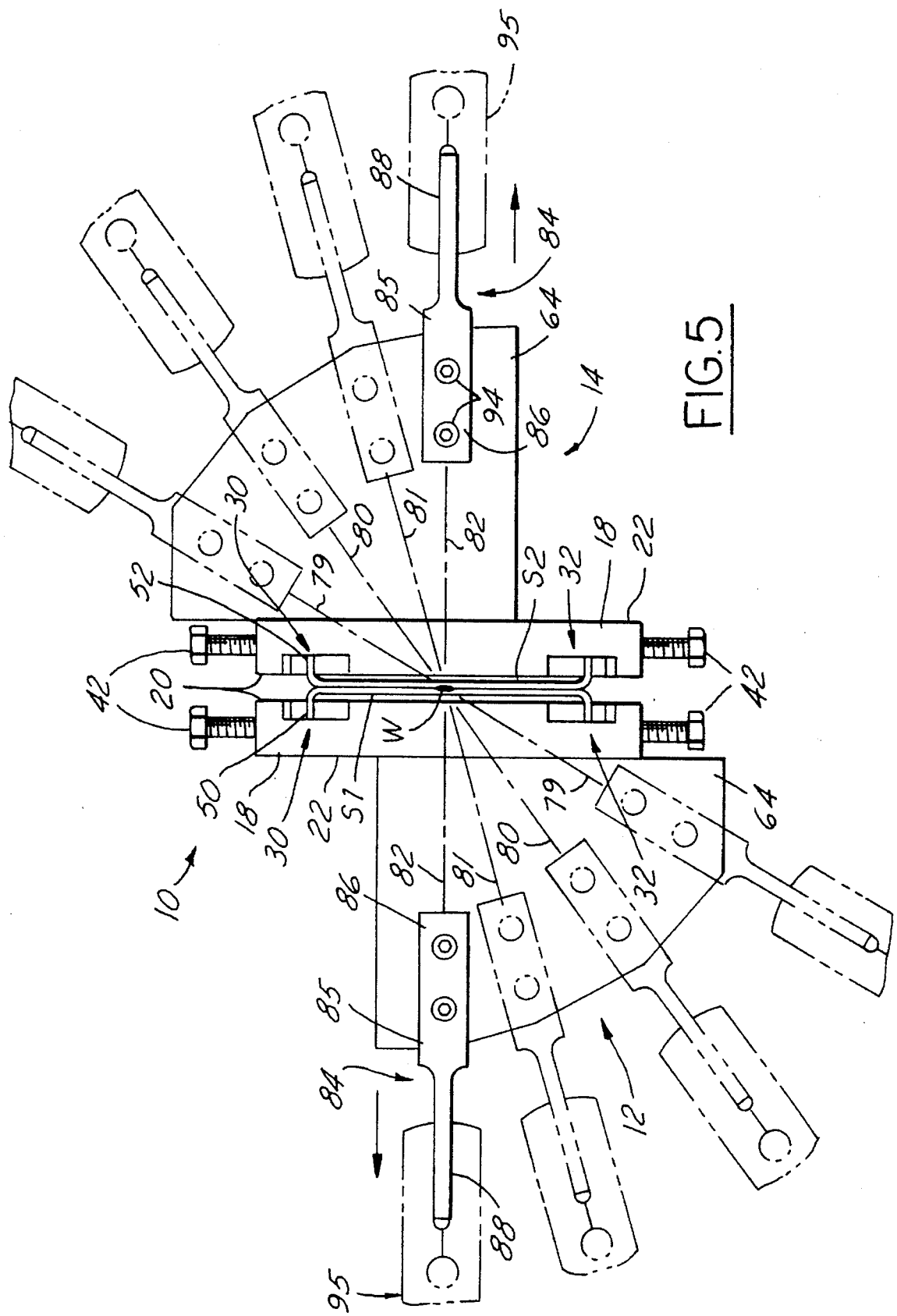
FIG. 5 is a side view of the test fixture in FIG. 1, showing several different positions of the pull bars.
Figure 7:
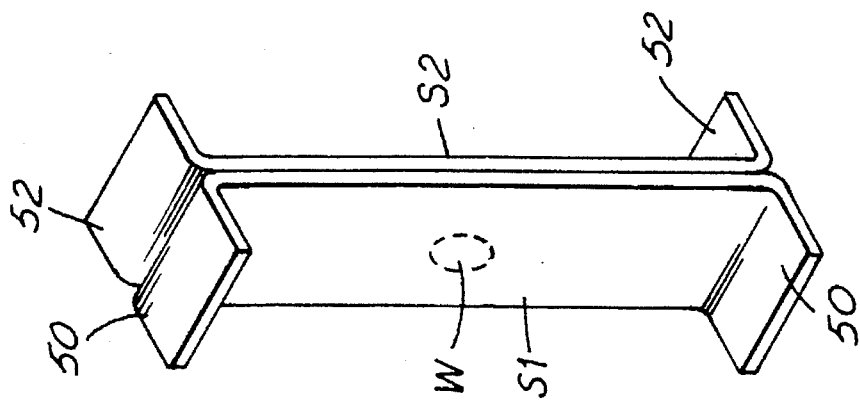
FIG. 7 is a perspective view of the two metal strips adapted to be tested.

The lock plate 64 of each test unit is formed with four pairs of spaced apart drilled holes. There are the pair of spaced apart drilled holes 71,72, the pair of spaced apart drilled holes 73,74, the pair of spaced apart drilled holes 75,76 and the pair of spaced apart drilled holes 77,78. The spacing of the holes of each pair is the same. Referring to FIG. 5, for each clamping frame, a straight line 79 drawn through the pair of drilled holes 71,72 forms an angle of approximately 30° to the front face of the fixture and also to the specimen plane; a straight line 80 drawn through the pair of holes 73,74 forms an angle of approximately 50° to the front face of the fixture and also to the specimen plane; a straight line 81 drawn through the pair of holes 75,76 forms an angle of approximately 70° to the front face and also to the specimen plane; and a straight line 82 drawn through the pair of holes 77,78 forms an angle of approximately 90° to the front face of the fixture and also to the specimen plane. The selected angles may vary, as desired. The lines 79–82 drawn through the pairs of holes are all designed to pass through the midpoint of the weld W of the strips S1 and S2 clamped to the test unit 12 and 14. The pairs of holes in each lock plate are intended to mount a pull bar in selected positions of adjustment as will now be described.

An elongated pull bar 84 is associated with each test unit 12,14. The pull bars are of identical construction, each having a forked end 85 consisting of a pair of prongs 86, and a stem 88 extending from the closed end of the fork. The forked end 85 is designed to straddle the lock plate. Each prong 86 of each pull bar has two longitudinally spaced apart holes 90,92 which are respectively aligned with similar holes in the other prong. The spacing of the holes 90,92 is the same as the spacing between the pairs of drilled holes in the lock plate. It is possible to mount each pull bar on the associated lock plate of each test unit by causing the forked end thereof to straddle the lock plate and aligning the holes in the prongs of the forked end with a pair of drilled holes in the lock plate and then inserting fasteners 94 through the aligned holes. The fasteners 94 may be in the form of bolts or screws with nuts threaded on the ends.

When the flanged ends of the metal strips are clamped respectively by the clamps 30,32 of the two test units, and with the pull bars installed in any pair of drilled holes in the lock plates, the pull bars will be aligned with one of the lines 79–82 passing through the weld. Obviously to perform a test, the two pull bars will be clamped to their respective lock plates in positions of alignment so that a suitable pulling mechanism 95 applied to the opposite ends of the pull bars will impose a pulling force which passes through the weld.

The outer end portions or stems 88 of the pull bars 84 are formed so as to be adapted to be grasped by the pulling mechanism 95 for applying a separating force on the strips.

In use, one test unit is turned 180° relative to the other with their front faces 20 in confronting relation. The strips S1 and S2 are placed between the clamping frames 18 of the two test units and the flanges 50 and 52 of the strips S1 and S2 are gripped between the clamping inserts of clamps 30 and 32 of the clamping frames by actuating the bolts 42. The pull bars 84 are secured to the lock plates 64 of each test unit in alignment with one another by the fasteners 94 extending through the holes in the prongs and an aligned pair of holes in the lock plates. The pull bars should be thus secured to the lock plates so that they are in the same angular positions, that is at the 30° position, the 50° position, the 70° position or the 90° position, so that they are in alignment with one another. Then a suitable pull mechanism grasps the outer end portions of the pull bars and a separating force is exerted thereon and, hence upon the weld. This force is increased until failure of the weld occurs. The force at failure of the weld can be determined by and recorded by suitable instrumentation associated with the pull mechanism.

Figure 8:
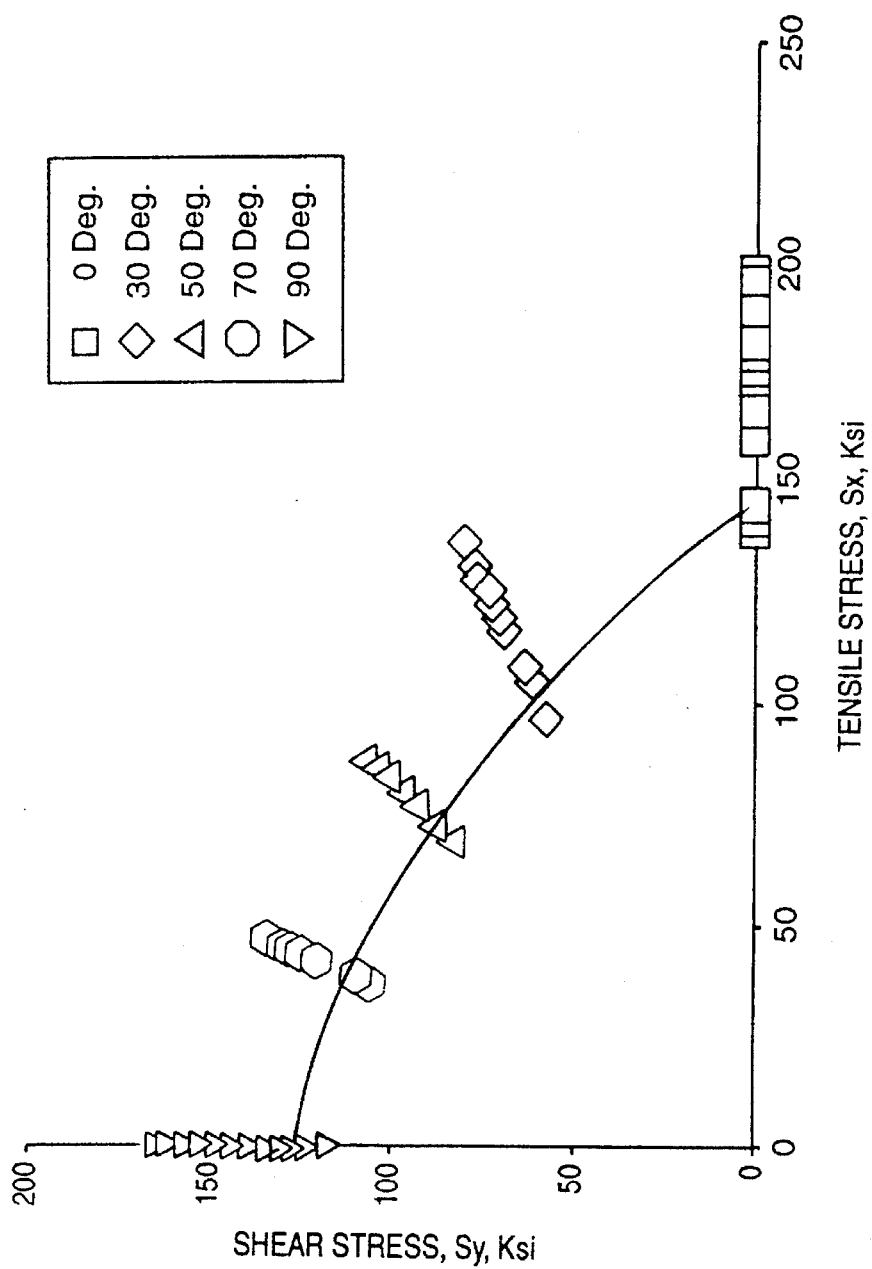
FIG. 8 is a diagram showing test results.

This procedure is followed with other welded strips similar to strips S1 and S2 at each of the four angular positions of attachment of the pull bars, the pull bars in each instance being in alignment. As will be appreciated, test strips of different widths fabricated from metal of different gages can be mounted in the fixture 10. The weld may also be tested in shear, that is at 0°, by a conventional testing machine. The forces at failure are plotted for each of the angular positions tested as shown in FIG. 8. The plotted points are formed according to the code associated with FIG. 8. A curve 98 through these plotted points encloses an area 99 which can be considered as safe for loads at forces within the area.

What is claimed is:

1. A fixture for testing the strength of a resistance spot weld connecting two overlapping, generally parallel first and second test strips, said fixture comprising first and second test units, said first test unit having a first clamping frame and said second test unit having a second clamping frame, said first clamping frame having a front face and a rear face and releasable first clamping means for gripping and holding the first test strip on the front face thereof, said second clamping frame having a front face and a rear face and releasable second clamping means for gripping and holding the second test strip on the front face thereof, a first elongated pull bar, means on the rear face of said first clamping frame mounting said first pull bar in selected angular positions extending rearwardly away from said first clamping frame, a second elongated pull bar, means on the rear face of said second clamping frame mounting said second pull bar in selected angular positions extending rearwardly away from said second clamping frame, the first pull bar in any of one of its selected angular positions being aligned with the second pull bar in one of its selected angular positions, said pull bars having end portions capable of being grasped by suitable pulling mechanism to apply a separating force on the strips.

2. A fixture as set forth in claim 1, wherein each of said pull bars in any of its respective selected angular positions extends on a line passing through the resistance spot weld so that when said pull bars are aligned and the end portions thereof are grasped by the pulling mechanism to apply a separating force on the strips, the separating force is on a line passing through the resistance spot weld.

3. A fixture as set forth in claim 2, wherein said means for mounting the first pull bar on the first clamping frame and the second pull bar on the second clamping frame comprises a first lock plate secured in perpendicular relation to the rear face of the first clamping frame, a second lock plate secured in perpendicular relation to the rear face of the said second clamping frame, and means for securing said first and second pull bars to said respective first and second lock plates in said selected angular positions.

4. A fixture as set forth in claim 3, wherein the clamping means for each of said frames comprises a pair of spaced apart clamps for clamping the opposite ends of one of the test strips, each said clamp comprising opposed clamping inserts having a predetermined height, one of which is seated on a fixed abutment of the associated clamping frame and the other of which is movable toward and away from the seated clamping insert, and an actuator for each of said clamps threaded to the associated clamping frame for moving the movable clamping insert toward and away from the seated clamping insert.

5. A fixture as set forth in claim 4, wherein the clamping inserts are removable to permit use of clamping inserts of different heights to allow test strips of various lengths to be tested to permit study of length effects on strength.

6. A fixture as set forth in claim 4, wherein said test units, including the clamping frames, pull bars, lock plates, clamps and actuators thereof, are substantially identical.

* * * * *

UNITED STATES PATENT AND TRADEMARK OFFICE
Certificate

Patent No. 5,602,341

Patented: February 11, 1997

On petition requesting issuance of a certificate for correction of inventorship pursuant to 35 U. S. C. 256, it has been found that the above-identified patent, through error and without deceptive intent, improperly sets forth the inventorship.

Accordingly, it is hereby certified that the correct inventorship of this patent is: Yung-Li Lee, Troy, Mich.; Timothy Wehner, Auburn Hills, Mich.; Thomas Morrissett, Troy, Mich.; Eric Pakalnins, Hartland, Mich.; Ming-Wei Lu, Ann Arbor, Mich.; and Chei-Long Tsai, Farmington Hills, Mich.

Signed and Sealed this Third Day of March, 1998.

RICHARD E. CHILCOT
*Supervisory Patent Examiner*
Art Unit 2214